(12) United States Patent
Rao et al.

(10) Patent No.: US 8,735,589 B2
(45) Date of Patent: May 27, 2014

(54) PROCESS FOR THE SYNTHESIS OF NARATRIPTAN

(75) Inventors: Dharmaraj Ramachandra Rao, Maharashtra (IN); Rajendra Narayanrao Kankan, Maharashtra (IN); Sandip Vasant Chikhalikar, Maharashtra (IN); Maruti Ghagare, Maharashtra (IN)

(73) Assignee: Cipla Limited, Mumbai (IN)

( * ) Notice: Subject to any disclaimer, the term of this patent is extended or adjusted under 35 U.S.C. 154(b) by 172 days.

(21) Appl. No.: 13/390,455

(22) PCT Filed: Aug. 18, 2010

(86) PCT No.: PCT/GB2010/001562
§ 371 (c)(1),
(2), (4) Date: May 1, 2012

(87) PCT Pub. No.: WO2011/021000
PCT Pub. Date: Feb. 24, 2011

(65) Prior Publication Data
US 2012/0220778 A1    Aug. 30, 2012

(30) Foreign Application Priority Data
Aug. 20, 2009 (IN) .......................... 1931/MUM/2009

(51) Int. Cl.
C07D 401/04 (2006.01)
C07C 255/50 (2006.01)

(52) U.S. Cl.
USPC .......................................... 546/201; 558/413

(58) Field of Classification Search
USPC .......................................... 546/201; 558/413
See application file for complete search history.

(56) References Cited

U.S. PATENT DOCUMENTS

| 4,997,841 | A | 3/1991 | Oxford et al. | |
| 5,786,473 | A | 7/1998 | Blatcher et al. | |
| 2007/0249649 | A1* | 10/2007 | Illig et al. | 514/278 |

FOREIGN PATENT DOCUMENTS

| EP | 0303507 | A2 | 2/1989 |
| WO | 2006010079 | A2 | 1/2006 |
| WO | 2008072257 | A2 | 6/2008 |
| WO | 2009118753 | A2 | 10/2009 |
| WO | 2011021000 | A2 | 2/2011 |

OTHER PUBLICATIONS

Layek et al. "Pd/C mediated synthesis . . . " Beil. zJ. Org. Chem. v.5(46) p. 1-9 (2009).*
Amjad, Muhammad, et al., "A Simple, Two-Step Synthesis of 3-Iodoindoles", Tetrahedron Letters, 2004, pp. 539-541, vol. 45, Elsevier Ltd.

Foreign communication from the priority application—International Search Report and Written Opinion, PCT/GB2010/001562 issued on Jul. 18, 2011, 15 pages.

* cited by examiner

*Primary Examiner* — Celia Chang
(74) *Attorney, Agent, or Firm* — Conley Rose, P.C.; Rodney B. Carroll

(57) ABSTRACT

The present invention relates to a process for preparing naratriptan or a salt thereof, the process comprising: (a) reacting a compound of formula (3) with a compound of the formula HCCR

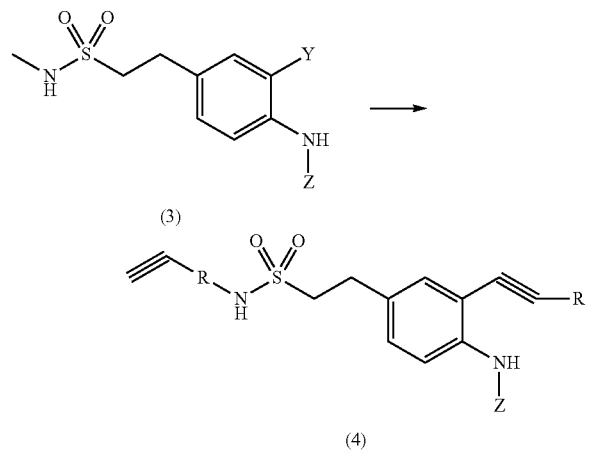

wherein Z is a protecting group, Y is a leaving group and R is a trialkyl silyl group, a trialkylstannyl group or a zinc (II) halide, to obtain the compound of formula (4); (b) converting the compound of formula (4) to a compound of formula (5)

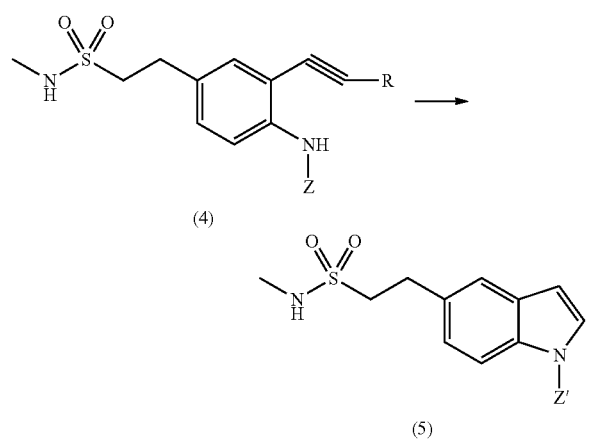

wherein Z' is hydrogen or a benzyl group; (c) converting the compound of formula (5) to naratriptan; and (d) optionally converting naratriptan to a salt thereof. The present invention also provides novel compounds (3) and (4) and processes for their preparation.

16 Claims, No Drawings

PROCESS FOR THE SYNTHESIS OF NARATRIPTAN

CROSS-REFERENCE TO RELATED APPLICATIONS

This application is a filing under 35 U.S.C. 371 of International Application No. PCT/GB2010/001562 filed Aug. 18, 2010, entitled "A Process for the Synthesis of Naratriptan," claiming priority of Indian Patent Application No. 1931/MUM/2009 filed Aug. 20, 2009, which applications are incorporated by reference herein in their entirety.

TECHNICAL FIELD OF THE INVENTION

The present invention relates to a process for the synthesis of naratriptan or salts thereof. The invention further relates to new intermediates, and processes for preparation thereof, for use in the synthesis of naratriptan.

BACKGROUND AND PRIOR ART

Naratriptan belongs to a family of tryptamine based drugs (triptans) used as selective (1B/1D) serotonin 5-hydroxytryptamine (5-HT) agonists. It is used in the treatment of migraine and cluster headaches. Its action is attributed to its binding to serotonin 5-$HT_{1B}$ and 5-$BT_{1D}$ receptors in cranial blood vessels (causing their constriction) and subsequent inhibition of pro-inflammatory neuropeptide release. It acts on serotonin receptors in nerve endings as well as the blood vessels. This leads to a decrease in the release of several peptides, including CGRP and substance P.

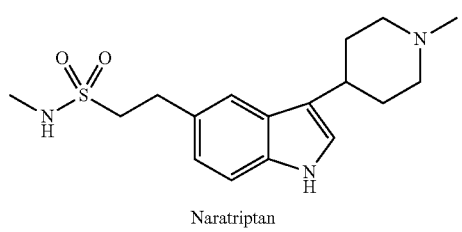

Naratriptan

U.S. Pat. No. 4,997,841 discloses naratriptan, its salts and several processes for its preparation. One of the processes comprises reacting 5-bromoindole with 1-methylpiperidin-4-one by means of KOH in methanol at room temperature to give 5-bromo-3-(4-(hydroxy-1-methylpiperidin-4-yl)-1H-indole, which is condensed with N-methylvinylsulfonamide by means of palladium acetate and tri-p-tolyl phosphine in hot DMF to afford (E)-N-methyl-2-[3-(1-methyl-1,2,3,6-tetrahydropyridin-4-yl)-1H-indol-5-yl]vinylsulfonamide. Finally, this compound is hydrogenated with $H_2$ over Pd/C to obtain naratriptan.

In another process as described in US '841, if the reaction of 5-bromoindole with 1-methylpiperidin-4-one by means of KOH in methanol is carried out at reflux temperature the resulting product is 5-bromo-3-(1-methyl-1,2,3,6-tetrahydropyridin-4-yl)-1H-indole which is further condensed with N-methylvinylsulfonamide as described above to obtain naratriptan.

Another process disclosed in US '841 comprises cyclization of 2-(4-hydrazinophenyl)-N-methylethanesulfonamide with 2-(1-methylpiperidin-4-yl)acetaldehyde by means of HCl in water.

U.S. Pat. No. 5,786,473 describes a reaction of 5-bromoindole with N-methyl-4-piperidone to obtain 5-bromo-3-(1-methyl-1,2,3,6-tetrahydropyridin-4-yl)-1H-indole which is condensed with N-methylvinylsulfonamide to afford N-methyl-2-[3-(1,2,3,6-tertahydro-1-methyl-4-pyridinyl)-1H-indol-5-yl]ethenesulfonamide which is reduced under heterogeneous hydrogenation conditions to obtain naratritpan.

WO2006010079 discloses the preparation of naratriptan based on the Japp-Klingemann reaction as a key step in building the indole moiety. The process comprises diazotizing N-methyl-2-(4-aminophenyl)-ethane sulfonamide with methyl-2-acetyl-3-pyridyl propanoate under Japp-Klingemann coupling to afford the corresponding hydrazone compound which is cyclised in the presence of an acid to afford methyl-5-methyl sulfamoylethyl-3-(4-pyridyl)-1H-2-indole carboxylate. It is quaternized using methyl iodide to obtain 1-methyl-4-(2-methoxy carbonyl-5-methyl sulfamoylethyl-1H-3-indolyl)pyridinium iodide followed by the further steps of reduction, saponification and decarboxylation to obtain naratriptan.

WO2008072257 teaches a process for the preparation of naratriptan comprising cyclizing 2-{[4-(2-methylsulfamoyl-ethyl)-phenyl]-hydrazono}-propionic acid ethyl ester to form 5-(2-methyl sulfamoyl-ethyl)-1-H-indole-2-carboxylic acid ethyl ester which is hydrolyzed to form 5-(2-methyl sulfamoyl-ethyl)-1-H-indole-2-carboxylic acid, followed by decarboxylation to obtain 5-(2-methyl sulfamoyl-ethyl)-1-H-indole. Further, this compound is condensed with N-methyl-4-piperidone to obtain 2-[3-(1-methyl-1,2,3,6-tetrahydro-pyridin-4-yl)-1H-indole-5yl]ethanesulfonic acid methyl amide followed by reduction to obtain naratriptan.

Naratriptan is a highly potent anti-migraine agent and there is a constant need for simpler and more industrially-applicable processes for its preparation. The inventors of the present invention aimed to develop such a process.

OBJECTS OF THE INVENTION

It is an object of the present invention to provide a process for the synthesis of naratriptan.

It is another object of the present invention to provide novel key intermediates useful in the synthesis of naratriptan.

SUMMARY OF THE INVENTION

According to a first aspect of the present invention, there is provided a process for preparing naratriptan or a salt thereof, the process comprising: (a) reacting a compound of formula (3) with a compound of the formula HCCR

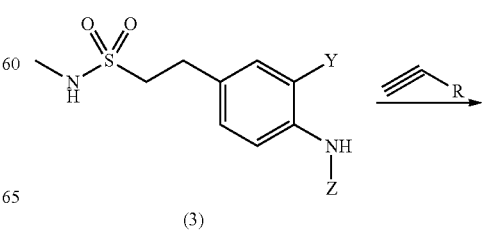

(3)

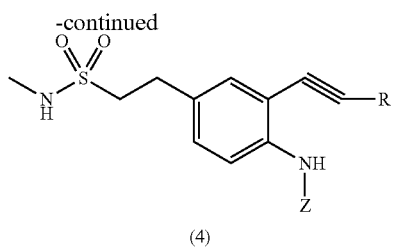

(4)

wherein Z is a protecting group, Y is a leaving group and R is a trialkyl silyl group, a trialkylstannyl group or a zinc (II) halide, to obtain the compound of formula (4); (b) converting the compound of formula (4) to a compound of formula (5)

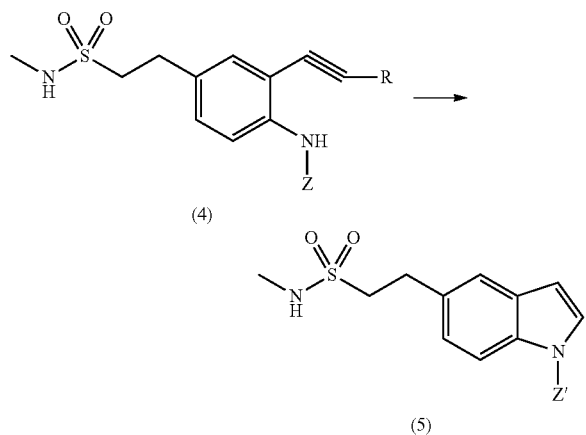

wherein Z' is hydrogen or a benzyl group, (c) converting the compound of formula (5) to naratriptan; and (d) optionally converting naratriptan to a salt thereof.

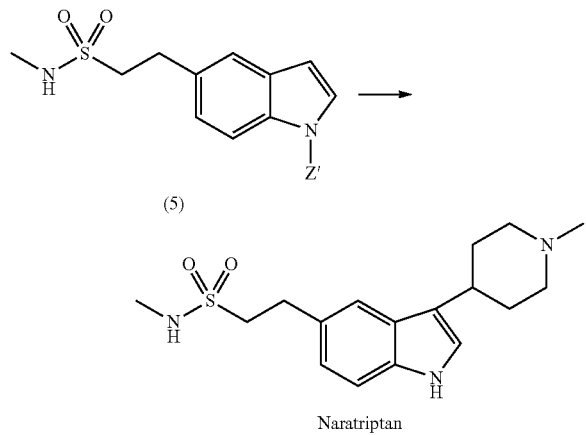

The salts of naratriptan are well known to those skilled in the art, as are the processes for preparing the salt from naratriptan. In an embodiment, the salt is the HCl salt. The HCl salt may be obtained by reacting the naratriptan with hydrochloric acid in a suitable solvent, such as methanol. The hydrochloric acid may be in the form of aqueous hydrochloric acid.

In an embodiment, the coupling reaction in step (a) is carried out by a Sonogashira reaction. The Sonogashira coupling involves coupling of the terminal alkyne of formula HCCR with compound (3) in the presence of a palladium catalyst, a copper (I) cocatalyst, and an amine base. The amine base may be triethyl amine, N,N-diisopropylethyl amine, diethylamine or trimethylamine. Preferably, the amine base is triethyl amine.

R may be a trialkyl silyl group. The alkyl may be a $C_1$-$C_6$ alkyl group, and all three alkyl groups may be the same or different. The alkyl group may be methyl, ethyl, propyl (i-propyl or n-propyl), butyl (t-butyl or n-butyl), pentyl or hexyl. For example, R may be ethyl dimethyl silyl, trimethyl silyl, triethyl silyl or diethyl methyl silyl.

R may be Sn(alkyl)$_3$. The alkyl may be a $C_1$-$C_6$ alkyl group, and all three alkyl groups may be the same or different. The alkyl group may be methyl, ethyl, propyl (i-propyl or n-propyl), butyl (t-butyl or n-butyl), pentyl or hexyl. For example, R may be thyl dimethyl stannyl, diethyl methyl stannyl or trimethyl stannyl.

R may be a zinc (II) halide, wherein halide is chloro, bromo or iodo. In an embodiment, R is —ZnBr.

The compound HCCR is a terminal alkyne having the formula.

The R group corresponds to the R group on compound (4). The compound HCCR is preferably selected from the group consisting of ethyl (ethynyl) dimethyl silane, trimethyl acetylene silane, triethyl (ethynyl) silane, diethyl (ethynyl)methyl silane, ethyl (ethynyl) dimethyl stannane, diethyl (ethynyl) methyl stannane, (ethynyl) trimethyl stannane and ethynyl zinc (II) halide. The corresponding R groups are ethyl dimethyl silyl, trimethyl silyl, triethyl silyl, diethyl methyl silyl, ethyl dimethyl stannyl, diethyl methyl stannyl, trimethyl stannyl and zinc (II) halide, respectively.

In an embodiment, Z is selected from the group consisting of acetyl, trifluoroacetyl, BOC (tert-butyloxycarbonyl), benzoyl, benzyloxy carbonyl (CBZ) and benzyl.

In an embodiment, Y is selected from the group consisting of chloro, bromo, iodo, OTf (triflate) and OTs (tosylate), preferably iodo.

In an embodiment, step (a) is carried out in the presence of a base, which may typically be an organic or an inorganic base. The inorganic base may be selected from potassium hydroxide, sodium hydroxide, calcium hydroxide, potassium carbonate, sodium carbonate, calcium carbonate, sodium bicarbonate, calcium carbonate, potassium carbonate, potassium ethoxide and sodium ethoxide. The organic base may be selected from pyridine, triethyl amine or N,N-diisopropylethyl amine, piperidine, diethylamine and trimethylamine. Preferably, the base is an organic base, most preferably triethyl amine.

In an embodiment, step (a) is carried out in the presence of a palladium-phosphine complex and optionally in the presence of a copper (I) halide and lithium halide. Preferably, the Pd-phosphine complex is tetrakistriphenylphosphine Pd (0).

In an embodiment, step (a) is carried out in the presence of a palladium-phosphine complex and a copper (I) halide and lithium halide. Preferably, the halide salt of copper is copper (I) iodide and that of lithium is chloride.

The solvent used for the step (a) is typically a polar solvent selected from water, acetone, acetonitrile, ethyl acetate, N,N-dimethylformamide, N-methylpyrrolidone, dimethylsulfoxide, sulfolane, a $C_{1-6}$ alcohol, tetrahydrofuran and an ether, such as diisopropyl ether or ethyl methyl ether. Preferably, the solvent is N,N-dimethylformamide.

In an embodiment, the process is carried out at a temperature ranging from 0° C. to the reflux temperature of the solvent used; preferably the reaction is carried out at a temperature ranging from 25° C. to 30° C.

In an embodiment, compound (4) is isolated, for example by using a solvent such as heptane, hexane, diisopropyl ether, water, ethyl acetate, toluene or xylene, most preferably heptane.

The conversion of compound (4) to compound (5) may proceed via direct conversion without isolation of any intermediate compounds. For example, when R is trialkylisilyl, the conversion may comprise desilylation of the R group, deprotection of the Z group and cyclisation to compound (5), all in one step. Alternatively, the conversion may comprise desilylation of the R group, with or without isolation of the desilylated intermediate compound, followed by simultaneous deprotection of the Z group and cyclisation. When both Z and Z' are benzyl groups, there is no need for deprotection of the Z group, so the conversion may comprise desilylation of the R group and cyclisation in one step or in separate steps.

In an embodiment, Z is a protecting group other than benzyl, Z' is hydrogen and the conversion of compound (4) to compound (5) comprises deprotection of group Z and cyclisation. Suitably, the deprotection is carried out using tetrabutylammonium halide or an acid selected from acetic acid, trifluoroacetic acid, dilute sulfuric acid, dilute hydrochloric acid and dilute nitric acid. The cyclisation is typically carried out in the presence of a base and a solvent to obtain compound (5). The cyclisation may proceed through the following intermediate compound (4b) which may be optionally isolated,

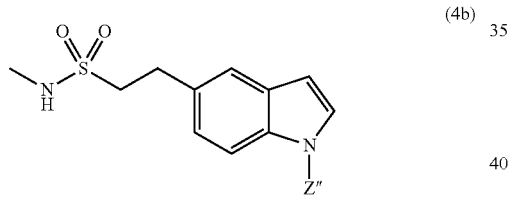

(4b)

wherein Z" is acetyl, trifluoroacetyl, BOC (tert-butyloxycarbonyl), benzoyl and benzyloxy carbonyl benzyl.

The base used for the cyclisation is typically an organic or an inorganic base. The inorganic base may be selected from potassium hydroxide, potassium tert-butoxide, sodium hydroxide, sodium methoxide, sodium ethoxide, calcium hydroxide, potassium carbonate, sodium carbonate or calcium carbonate. The organic base may be selected from pyridine, triethyl amine, N,N-diisopropylethyl amine, piperidine, diethylamine, trimethylamine, guanidine and lithium diisopropyl amide. Preferably, the base is potassium hydroxide.

The solvent used for the cyclisation may be selected from dichloromethane, ethylene dichloride, toluene, benzene, xylene, ethyl acetate, sulfolane, dimethylacetamide, dimethylsulfoxide, N,N-dimethylformamide, N-methylpyrrolidone, diglyme, heptane, hexane, a $C_{1-6}$ alcohol, diethyl ether, diisopropyl ether, diethyl ether or mixtures thereof, most preferably N-methylpyrrolidone.

In an embodiment, the process is carried out at a temperature ranging from 0° C. to the reflux temperature of the solvent used. Suitably, the temperature ranges from 20° C. to the reflux temperature, preferably from 50° C. to 90° C., more preferably from 70° C. to 90° C. Most preferably, the temperature ranges from 80° C. to 90° C.

In an embodiment, Z is benzyl and Z' is benzyl, and the conversion of compound (4) to compound (5) comprises cyclising compound (4) in the presence of a base and a solvent.

The base used for the cyclisation may be selected from The base may be selected from potassium hydroxide, potassium tert-butoxide, sodium hydroxide, sodium methoxide, sodium ethoxide, calcium hydroxide, potassium carbonate, sodium carbonate or calcium carbonate. Preferably, the base is potassium tert-butoxide.

Compound (5) may be isolated by treating with a solvent such as ether, diisopropyl ether, diethylether, t-butyl methyl ether, a $C_{1-6}$ alcohol, water, toluene, xylene, ethyl acetate, heptane or hexane.

In an embodiment, conversion of compound (5) to naratriptan comprises reacting compound (5) with N-methyl-4-piperidone to form a compound of formula (6) and converting compound (6) to naratriptan.

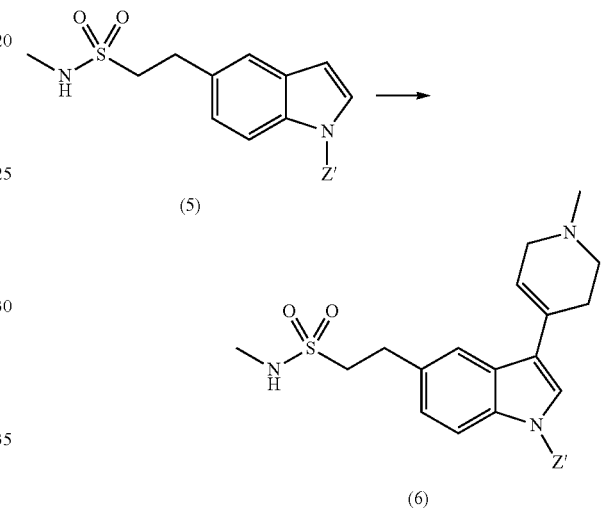

In an embodiment, the conversion is carried out in the presence of either a base such as KOH, potassium ter-butoxide or sodium hydride or in the presence of a trihaloacetic acid such as trifluoroacetic acid or trichloroacetic acid.

Typically, the conversion is carried out via an Aldol condensation to obtain the corresponding condensation product of formula (6). Optionally, the compound of formula (6) is isolated.

The solvent used for the conversion is typically methylated spirit, methanol, ethanol, isopropanol dimethylsulfoxide, N,N-dimethylformamide or N-methylpyrrolidone or mixtures thereof, preferably methanol.

The condensation is typically carried out at the reflux temperature of the solvent used.

In an embodiment, compound (6) is reduced either by catalytic hydrogenation or by organic reduction to obtain naratriptan which may be optionally converted to its salt.

In an embodiment, Z' is hydrogen and the conversion of compound (6) to naratriptan comprises catalytic hydrogenation in the presence of a catalyst selected from the group consisting of palladium, palladium hydroxide, palladium on activated carbon, palladium on alumina, platinum, platinum on activated carbon, ruthenium, rhodium and Raney nickel.

The solvent used for the hydrogenation is typically selected from methanol, ethanol, isopropyl alcohol, dioxane, N,N-dimethylformamide, diethyl ether, diisopropyl ether, t-butyl methyl ether, tetrahydrofuran, ethyl acetate, methylene chloride, ethylene chloride or mixtures thereof, preferably methanol.

The source of hydrogen is hydrogen gas. The reduction reaction is typically carried out at a hydrogen gas pressure ranging from about 25 psi to about 80 psi (from about 170 kPa to about 550 kPa), preferably from about 55 psi to about 60 psi (from about 380 kPa to about 410 kPa).

Alternatively, when Z' is hydrogen, the reduction of compound (6) may be carried out by organic reduction. The organic reduction may be carried out treating the compound (6) with a trialkyl silane, preferably triethyl silane.

In an embodiment, Z' is benzyl and the conversion of compound (6) to naratriptan comprises organic reduction. The organic reduction may be carried out by treating the compound (6) with a trialkyl silane, preferably triethyl silane.

The solvent used for the organic reduction is typically a non-polar solvent such as xylene, toluene, N,N-dimethylformamide, N-methylpyrrolidone or mixtures thereof, most preferably toluene.

In an embodiment, the organic reduction is carried out at a temperature ranging from −20° C. to the reflux temperature of the solvent.

In an embodiment, compound (6) is first reduced by organic reduction in situ to obtain compound (7) which further undergoes catalytic hydrogenation to obtain naratriptan.

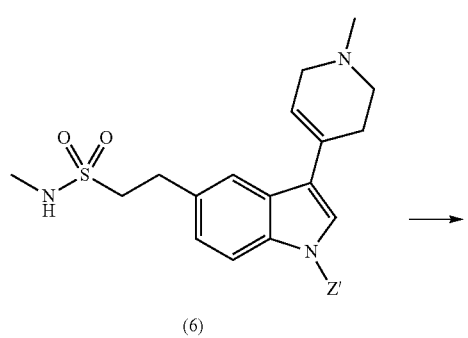

(6)

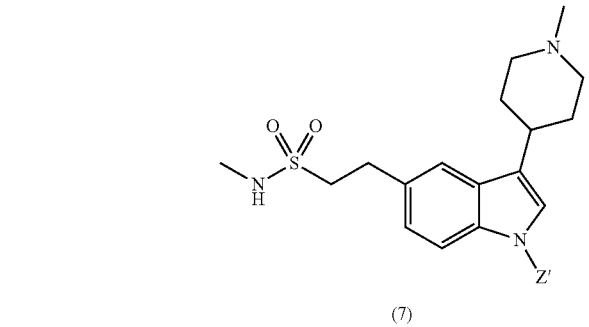

(7)

According to another aspect of the present invention, there is provided a compound of formula (3)

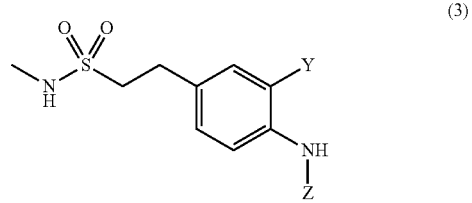

(3)

wherein Z is selected from the group consisting of acetyl, trifluoroactyl, BOC, benzoyl, benzyloxy carbonyl and benzyl, and Y is selected from the group consisting of chloro, bromo, iodo, OTf (triflate) and OTs (tosylate). In an embodiment, Z is benzyl. In an embodiment, Y is iodo.

According to another aspect of the present invention, there is provided the use of compound (3) in a process for preparing naratriptan or a salt thereof.

According to another aspect of the present invention, there is provided a process for preparing a compound of formula (3) comprising reacting a compound of formula (2) with an N-protecting agent corresponding to the protecting group Z.

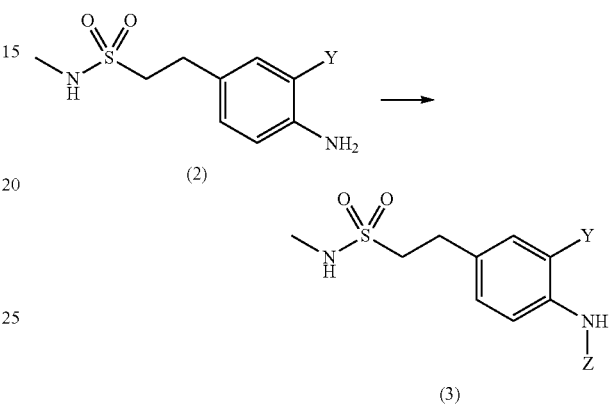

(2)

(3)

In an embodiment, the N-protecting agent is an aliphatic or an aromatic compound. The agent may be selected from the group consisting of acetic anhydride, trifluoroacetic anhydride, trifluoroacetyl chloride, BOC-anhydride, benzyloxy carbonyl chloride, benzoyl chloride and benzyl chloride optionally-substituted, for example with a group selected from methoxy, tosylate or a halide such as chloro.

Preferably, the aliphatic N-protecting agent is acetic anhydride. Preferably, the aromatic N-protecting agent is benzyl chloride.

Suitably, the process is carried out in the presence of a solvent selected from dichloromethane, a $C_{1-6}$ alcohol, ethylene dichloride, toluene, benzene, xylene, ethyl acetate, sulfolane, dimethylacetamide, dimethylsulfoxide, N,N-dimethylformamide, N-methylpyrrolidone, diglyme or mixtures thereof. Preferably, the solvent is dichloromethane.

The process is typically carried out at a temperature ranging from 0° C. to the reflux temperature of the solvent used, preferably at a temperature ranging from 25° C. to 30° C.

In an embodiment, the compound of formula (3) is isolated, for example using a solvent such as hexane, heptane or a $C_{1-6}$ alcohol.

In an embodiment, the compound of formula (2) is prepared by reacting a compound of formula (1) with a reagent that generates the leaving group Y.

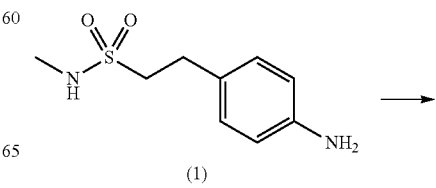

(1)

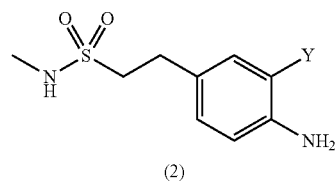

(2)

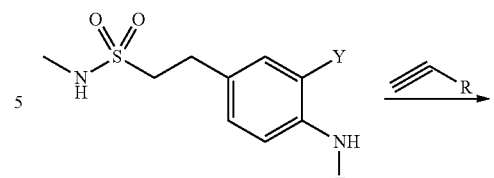

(3)

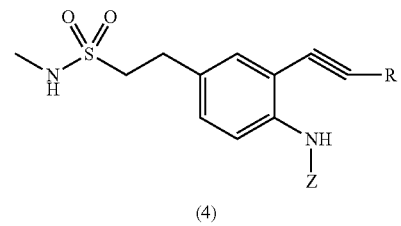

(4)

The reagent may be selected from N-chlorosuccinimide, chlorine, bromine, potassium bromide, N-bromosuccinimide, iodine, potassium iodide, iodine monochloride, triflic acid and p-toluene sulphonic acid.

The reaction may be carried out in the presence of a base; typically an organic or an inorganic base. The inorganic base may be selected from potassium hydroxide, sodium hydroxide, calcium hydroxide, potassium carbonate, sodium carbonate, calcium carbonate and sodium bicarbonate. The organic base may be selected from pyridine, triethyl amine, N,N-diisopropylethyl amine, piperidine, diethylamine and trimethylamine. Preferably, the base is sodium bicarbonate.

Typically, a solvent for use in the reaction is dichloromethane, ethyl acetate, toluene, xylene, tetrahydrofuran, 2-methyltetrahydrofuran, sulfolane, dimethylacetamide, dimethylsulfoxide, N-methylpyrrolidone, diglyme, or mixtures thereof, most preferably dichloromethane.

Typically, the process is carried out at a temperature ranging from 0° C. to the reflux temperature of the solvent used; preferably the reaction is carried out at a temperature ranging from 25° C. to 30° C.

In an embodiment, compound (2) is isolated, for example by treating with a solvent such as hexane, heptane, pentane, water, ethyl acetate, toluene, xylene, cyclohexane or mixtures thereof, preferably heptane is used.

The process for preparing naratriptan or salts thereof, as described above, may comprise preparing compound (3) as described above.

According to another aspect of the present invention, there is provided a compound of formula (4)

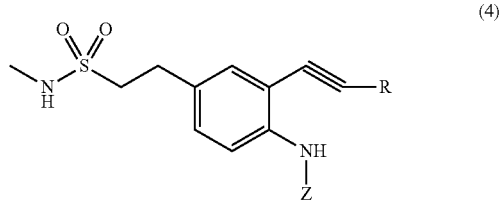

(4)

wherein Z is selected from the group consisting of acetyl, trifluoroactyl, BOC, benzoyl, benzyloxy carbonyl and benzyl, and R is selected from the group consisting of trimethylsilyl, —Sn(Bu)$_3$ or —ZnBr. In an embodiment, Z is benzyl.

According to another aspect of the present invention, there is provided a process for preparing a compound of formula (4), the process comprising reacting a compound of formula (3) with a compound of the formula HCCR wherein Z is selected from the group consisting of acetyl, trifluoroactyl, BOC, benzoyl, benzyloxy carbonyl and benzyl, Y is a leaving group and R is trimethylsilyl, —Sn(Bu)$_3$ or —ZnBr.

In an embodiment, Y is selected from the group consisting of chloro, bromo, iodo, OTf (triflate) and OTs (tosylate), preferably iodo.

In an embodiment, the reaction is carried out by a Sonogashira reaction. The Sonogashira coupling involves coupling of the terminal alkyne of formula HCCR with compound (3) in the presence of a palladium catalyst, a copper (I) cocatalyst, and an amine base. The amine base may be triethyl amine, N,N-diisopropylethyl amine, diethylamine or trimethylamine. Preferably, the amine base is triethyl amine.

In an embodiment, the reaction is carried out in the presence of a base, which may typically be an organic or an inorganic base. The inorganic base may be selected from potassium hydroxide, sodium hydroxide, calcium hydroxide, potassium carbonate, sodium carbonate, calcium carbonate, sodium bicarbonate, calcium carbonate, potassium carbonate, potassium ethoxide and sodium ethoxide. The organic base may be selected from pyridine, triethyl amine or N,N-diisopropylethyl amine, piperidine, diethylamine and trimethylamine. Preferably, the base is an organic base, most preferably triethyl amine.

In an embodiment, the reaction is carried out in the presence of a palladium-phosphine complex and optionally in the presence of a copper (I) halide and lithium halide. Preferably, the Pd-phosphine complex is tetrakistriphenylphosphine Pd (0).

In an embodiment, the reaction is carried out in the presence of a palladium-phosphine complex and a copper (I) halide and lithium halide. Preferably, the halide salt of copper is copper (I) iodide and that of lithium is chloride.

The solvent used is typically a polar solvent selected from water, acetone, acetonitrile, ethyl acetate, N,N-dimethylformamide, N-methylpyrrolidone, dimethylsulfoxide, sulfolane, a $C_{1-6}$ alcohols, tetrahydrofuran and an ether, such as diisopropyl ether or ethyl methyl ether. Preferably, the solvent is N,N-dimethylformamide.

In an embodiment, the process is carried out at a temperature range from 0° C. to the reflux temperature of the solvent used; preferably the reaction is carried out at a temperature ranging from 25° C. to 30° C.

In an embodiment, compound (4) is isolated, for example by using a solvent such as heptane, hexane, diisopropyl ether, water, ethyl acetate, toluene or xylene, most preferably heptane.

The process for preparing compound (4), as described above, may further comprise preparing compound (3) as described above.

According to another aspect of the present invention, there is provided the use of compound (4) in a process for preparing naratriptan or a salt thereof.

Certain embodiments of compounds (2), (5), (6) and (7) are advantageous, for example because they are preferred compounds for use in the process for preparing naratriptan as described above. These preferred compounds are discussed below.

According to another aspect of the present invention, there is provided a compound of formula (2), wherein Y is iodo. This compound shall be referred to as compound (2a). According to another aspect of the present invention, there is provided the use of compound (2a) in a process for preparing naratriptan or a salt thereof. The process may involve the process described above.

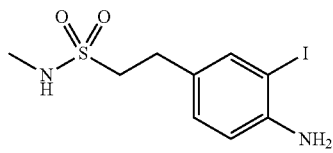

(2a)

According to another aspect of the present invention, there is provided a compound of formula (5), wherein Z' is benzyl. This compound shall be referred to as compound (5b). According to another aspect of the present invention, there is provided the use of compound (5b) in a process for preparing naratriptan or a salt thereof. The process may involve the process described above.

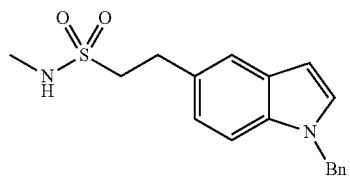

(5b)

According to another aspect of the present invention, there is provided a compound of formula (6), wherein Z' is benzyl. This compound shall be referred to as compound (6a). According to another aspect of the present invention, there is provided the use of compound (6a) in a process for preparing naratriptan or a salt thereof. The process may involve the process described above.

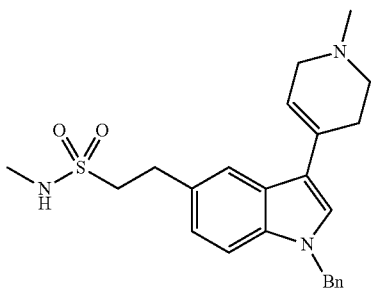

(6a)

According to another aspect of the present invention, there is provided a compound of formula (7), wherein Z' is benzyl. This compound shall be referred to as compound (7a). According to another aspect of the present invention, there is provided the use of compound (7a) in a process for preparing naratriptan or a salt thereof. The process may involve the process described above.

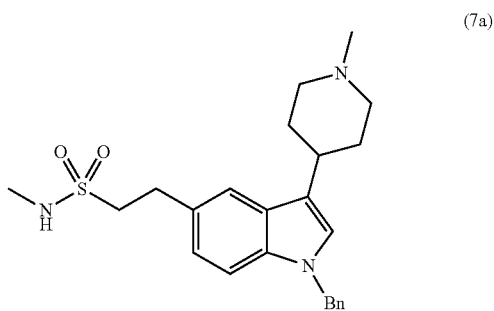 [SMILES: CNS(=O)(=O)CCc1ccc2c(c1)c(C1CCN(C)CC1)cn2Cc1ccccc1]

(7a)

According to another aspect of the present invention, there is provided naratriptan prepared by a process described above.

According to another aspect of the present invention, there is provided naratriptan prepared by a process described above for use in medicine.

According to another aspect of the present invention, there is provided the use of naratriptan prepared by a process described above for use in the manufacture of a medicament for treating migraine or cluster headaches.

According to another aspect of the present invention, there is provided a method of treating migraine or cluster headaches in a patient in need thereof comprising administering to said patient naratriptan prepared by a process described above.

DETAILED DESCRIPTION OF THE INVENTION

Naratriptan contains an indole moiety in its structural formula. The present invention provides an indole derivative as an important intermediate of naratriptan. It is represented as follows as the compound of formula (5).

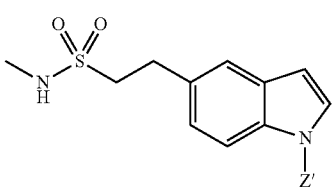

(5)

(5a) when Z'=H or (5b) when Z'=benzyl group

In an embodiment, there is provided a process for preparing a compound of formula (5) as described in Scheme I.

Scheme I

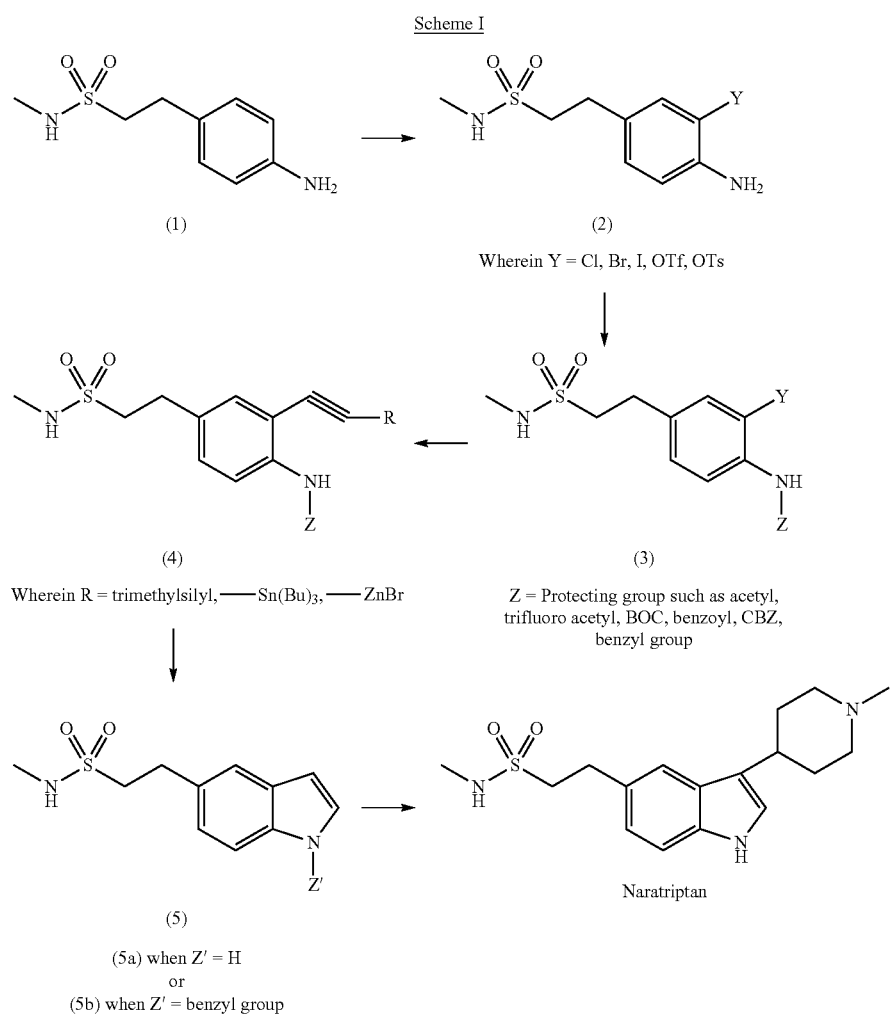

Naratriptan (5a) when Z' = H
or
(5b) when Z' = benzyl group

In an embodiment, there is provided a process for the preparation of compound (2) comprising treating a compound of formula (1) with a suitable reagent that generates a suitable leaving group Y.

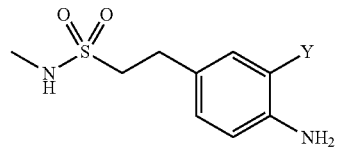

The suitable reagent may be selected from N-chlorosuccinimide, chlorine, bromine, potassium bromide, N-bromosuccinimide, iodine, potassium iodide, iodine monochloride, triflic acid and p-toluene sulphonic acid.

The suitable reagent generates a desired leaving group Y such as Cl, Br, I, OTf (triflate), OTs (tosylate). The preferable leaving group is iodo (I).

The base used may be an organic or an inorganic base. The inorganic base is selected from potassium hydroxide, sodium hydroxide, calcium hydroxide, potassium carbonate, sodium carbonate, calcium carbonate, sodium bicarbonate. The organic base may be selected from pyridine, triethyl amine, N,N-diisopropylethyl amine, piperidine, diethylamine or trimethylamine. The preferable base is sodium bicarbonate.

The suitable solvent used may be dichloromethane, ethyl acetate, toluene, xylene, tetrahydrofuran, 2-methyltetrahydrofuran, sulfolane, dimethylacetamide, dimethylsulfoxide, N-methylpyrrolidone, diglyme, or mixtures thereof, most preferably dichloromethane.

Typically, the process is carried out at a suitable temperature in the range of 0° C. to the reflux temperature of the solvent used; preferably the reaction is carried out at 25-30° C.

The compound of formula (2) can be optionally isolated for example by treating with a solvent such as hexane, heptane, pentane, water, ethyl acetate, toluene, xylene, cyclohexane or mixtures thereof, preferably heptane is used.

In an embodiment of the present invention, the compound of formula (2) is treated with a suitable N-protecting agent to obtain a novel compound of formula (3).

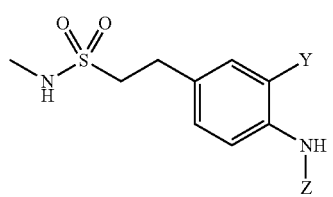

The suitable N-protecting agent may be selected from a group of aliphatic or aromatic compounds such as acetic anhydride, trifluoroacetic anhydride, trifluoroacetyl chloride, BOC-anhydride, benzyloxy carbonyl chloride, benzoyl chloride, benzyl chloride optionally substituted with groups such as chloro, methoxy, tosylate. The preferable aliphatic N-protecting agent is acetic anhydride and preferable aromatic N-protecting agent is benzyl chloride.

Z is the protecting group such as acetyl, trifluoroactyl, BOC, benzoyl, benzyloxy carbonyl, benzyl group derived from the corresponding protecting agents.

Suitably, the process is carried out in the presence of a solvent selected from dichloromethane, $C_{1-6}$ alcohols, ethylene dichloride, toluene, benzene, xylene, ethyl acetate, sulfolane, dimethylacetamide, dimethylsulfoxide, N,N-dimethylformamide, N-methylpyrrolidone, diglyme or mixtures thereof, preferably dichloromethane.

The process is carried out at a suitable temperature in the range of 0° C. to the reflux temperature of the solvent used, preferably at a temperature range of 25-30° C.

The compound of formula (3) can be isolated using a solvent such as hexane, heptane and $C_{1-6}$ alcohols.

In an embodiment, the compound of formula (2) is prepared by the process described herein above.

In another embodiment of the present invention, there is provided a process for preparation of a novel compound of formula (4).

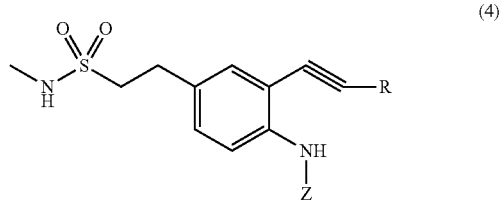

(4)

The process comprises treating the compound (3) with a compound having a terminal alkyne group represented by following structure to obtain the compound of formula (4).

Wherein R=trimethylsilyl, —Sn(Bu)$_3$, —ZnBr

Typically, the coupling reaction is carried out by a Sonogashira reaction.

The suitable coupling agent may be selected from terminal alkynes such as ethyl (ethynyl) dimethyl silane, trimethylsilyl acetylene, triethyl (ethynyl) silane, diethyl (ethynyl) methyl silane, ethyl (ethynyl) dimethyl stannane, diethyl (ethynyl) methyl stannane, (ethynyl) trimethyl stannane, ethynyl zinc (II) halide, most preferably, trimethylsilyl acetylene.

The base used may be an organic or an inorganic base. The inorganic base is selected from potassium hydroxide, sodium hydroxide, calcium hydroxide, potassium carbonate, sodium carbonate, calcium carbonate, sodium bicarbonate, calcium carbonate, potassium carbonate, potassium ethoxide, sodium ethoxide. The organic base may be selected from pyridine, triethyl amine or N,N-diisopropylethyl amine, piperidine, diethylamine, trimethylamine. The preferable base is an organic base, most preferably triethyl amine.

Typically, the coupling reaction takes place in the presence of Palladium (Pd)-phosphine complex and optionally in the presence of a copper (I) halide and lithium halide.

The preferable Pd-phosphine complex is tetrakistriphenylphosphine Pd (0).

Preferable halide salt of copper is copper (I) iodide and that of lithium is chloride.

The solvent used for the coupling is a polar solvent selected from water, acetone, acetonitrile, ethyl acetate, N,N-dimethylformamide, N-methylpyrrolidone, dimethylsulfoxide, sulfolane, $C_{1-6}$ alcohols, tetrahydrofuran, ethers such as diisopropyl ether, ethyl methyl ether, preferably N,N-dimethylformamide.

The process is carried out at a suitable temperature in the range of 0° C. to the reflux temperature of the solvent used; preferably the reaction is carried out at 25-30° C.

The compound (4) can be isolated for example by using a solvent such as heptane, hexane, diisopropyl ether, water, ethyl acetate, toluene or xylene, most preferably heptane.

In an embodiment, the compound of formula (4) is further cyclised by the process as represented in Scheme II below. The compound (4) is deprotected using tetrabutylammonium halide or an acid such as acetic acid, trifluoroacetic acid, dilute sulfuric acid, dilute hydrochloric acid, dilute nitric acid to obtain compound (4a) which is then cyclised in the presence of a base and a solvent to obtain compound (5).

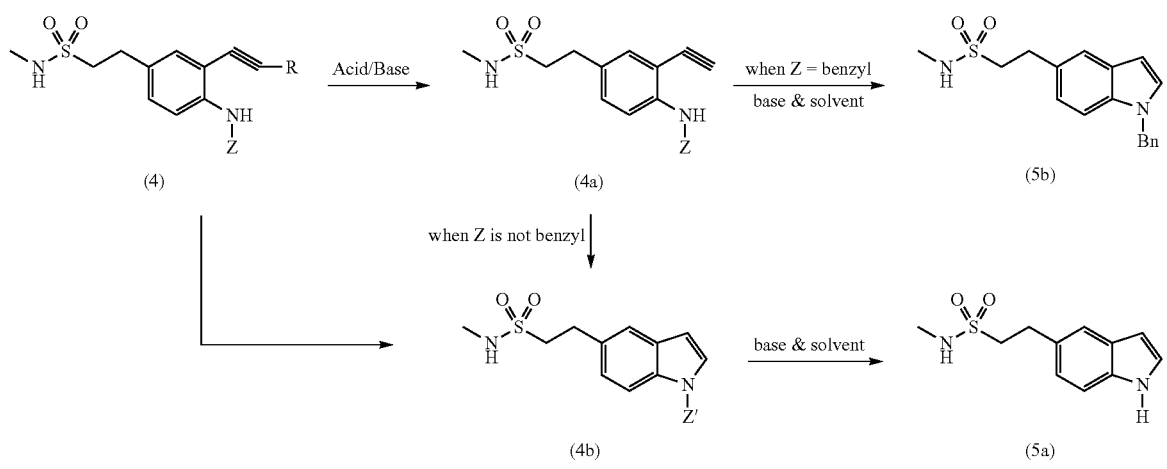

Scheme II

The base used may be an organic or an inorganic base. The inorganic base is selected from potassium hydroxide, potassium tert-butoxide, sodium hydroxide, sodium methoxide, sodium ethoxide, calcium hydroxide, potassium carbonate, sodium carbonate, calcium carbonate. The organic base may be selected from pyridine, triethyl amine or N,N-diisopropylethyl amine, piperidine, diethylamine, trimethylamine, guanidine, lithium diisopropyl amide. The preferable base is potassium hydroxide.

The suitable solvent used may be selected from dichloromethane, ethylene dichloride, toluene, benzene, xylene, ethyl acetate, sulfolane, dimethylacetamide, dimethylsulfoxide, N,N-dimethylformamide, N-methylpyrrolidone, diglyme, heptane, hexane, $C_{1-6}$ alcohol, diethyl ether, diisopropyl ether, diethyl ether or mixtures thereof, most preferably N-methylpyrrolidone.

The process is carried out at a suitable temperature in the range of 0° C. to the reflux temperature of the solvent used. Preferably, the temperature is in the range of 80-90° C.

Alternatively, compound (4) is cyclised in the presence of base and solvent to obtain compound of formula (5) directly without isolation of the compound of formula (4a).

The base used for the direct cyclisation is selected from inorganic bases as described hereinbefore. The preferable base is potassium tert-butoxide.

The cyclisation as described in the Scheme II is advantageous as the isolation of compound (4a) minimizes generation of impurities thereby resulting in compound of formula (5) with good yield and purity.

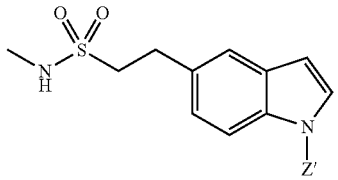

(5)

The compound (5) can be isolated by treating with a solvent such as ether, diisopropyl ether, diethylether, t-butyl methyl ether, $C_{1-6}$ alcohols, water, toluene, xylene, ethyl acetate, heptane, hexane.

The compound (5) obtained by the process of the present invention is further used in synthesis of naratriptan as shown in Scheme III below.

Scheme III

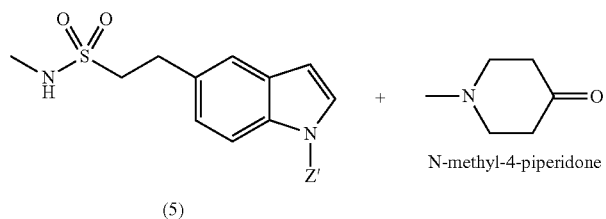

(5)    N-methyl-4-piperidone

Aldol condensation

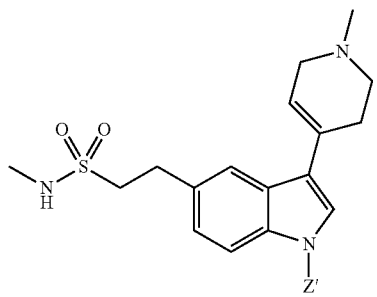

(6)

z' = benzyl gr.        z' = H

Et₃SiH                 H₂ Pd/C or Et₃SiH

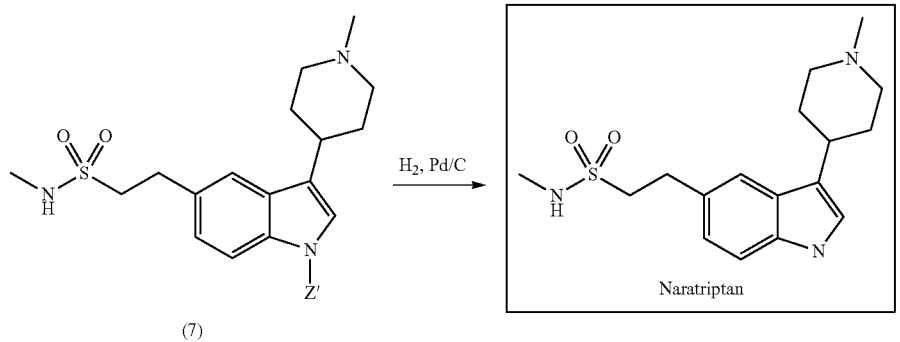

(7)                        Naratriptan

The compound (5) is further treated with N-methyl-4-piperidone in the presence of a strong base such as KOH, potassium ter-butoxide or sodium hydride or in the presence of a trihaloacetic acid such as trifluoroacetic acid or trichloroacetic acid via Aldol condensation to obtain corresponding condensation product of formula (6). The compound of formula (6) can be optionally isolated.

The solvent used can be methylated spirit, methanol, ethanol, isopropanol dimethylsulfoxide, N,N-dimethylformamide or N-methylpyrrolidone or mixtures thereof, preferably methanol.

The condensation is carried out at the reflux temperature of the solvent used.

Further, compound (6) is reduced either by catalytic hydrogenation or by organic reduction to obtain naratriptan which may be optionally converted to its salt.

The catalytic hydrogention is carried out in the presence of a catalyst selected from the group consisting of palladium, palladium hydroxide, palladium on activated carbon, palladium on alumina, platinum, platinum on activated carbon, ruthenium, rhodium and Raney nickel.

The solvent used for the hydrogenation is selected from methanol, ethanol, isopropyl alcohol, dioxane, N,N-dimethylformamide, diethyl ether, diisopropyl ether, t-butyl methyl ether, tetrahydrofuran, ethyl acetate, methylene chloride, ethylene chloride or mixtures thereof, preferably methanol.

The source of hydrogen is hydrogen gas. The reduction reaction is carried out at a hydrogen gas pressure ranging from about 25 psi to about 80 psi, preferably from about 55 psi to about 60 psi.

Alternatively, the reduction may be carried out by organic reduction. The organic reduction may be carried out treating the compound (6) with a trialkyl silane, preferably triethyl silane.

Suitably, the solvents used for reduction are non-polar solvents such as xylene, toluene, N,N-dimethylformamide, N-methylpyrrolidone or mixtures thereof, most preferably toluene.

The organic reduction is carried out in the temperature range of −20° C. to the reflux temperature of the solvent.

In an embodiment wherein, Z' is a benzyl group, the compound of formula (6) is first reduced by organic reduction in situ to obtain compound (7) which further undergoes catalytic hydrogenation to obtain naratriptan.

A skilled person may efficiently use the teachings of the present invention for synthesis of other triptans, such as zolmitriptan, sumatriptan, eletriptan, avitriptan and rizatriptan with high yields and purity.

EXAMPLES

The invention will now be illustrated further in relation to the following examples without restricting the scope of the invention in any way.

Example 1

Preparation of 2-(4-amino-3-iodo-phenyl)-ethanesulfonic Acid Methylamide

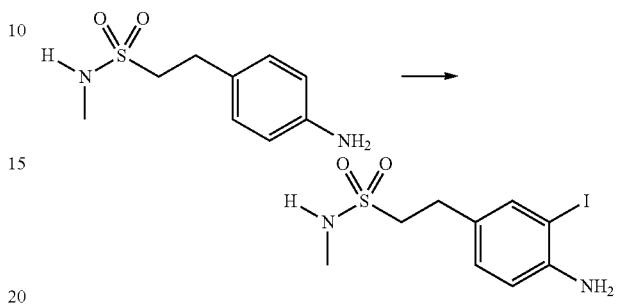

A solution of 2-(4-aminophenyl)ethane sulfonic acid methylamide (100 g) in dichloromethane (1000 ml) was prepared and 10% solution of sodium bicarbonate (1000 ml) was added at 25° C. so as to obtain a biphasic reaction mass. Iodine crystals were added slowly maintaining the temperature below 30° C. The mixture was agitated at 25° C. for about 60 minutes and cooled to 10-15° C. The excess of iodine content in the mixture was neutralized with saturated sodium metabisulphite solution and subjected to vacuum distillation. The residue so obtained was agitated with heptane to give the title compound. (Yield: 150 g, HPLC Purity: 99.9%).

Example 2

Preparation of N-[2-iodo-4-(2-methylsulfamoyl-ethyl)-phenyl]-acetamide

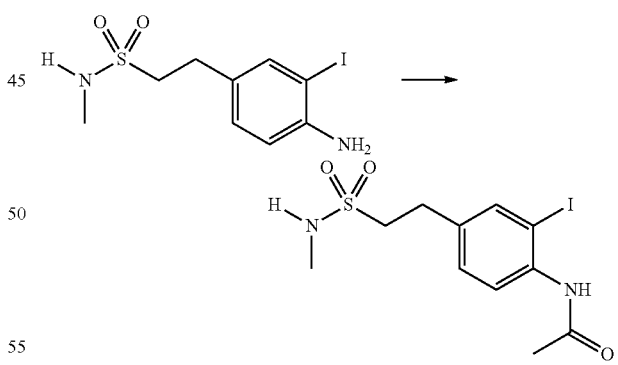

A solution of 2-(4-amino-3-iodo-phenyl)-ethanesulfonic acid methylamide (150 g) in dichloromethane (1500 ml) was prepared. A 50% solution of acetic anhydride in dichloromethane (600 ml) was added at 25° C. The reaction mass was stirred for about 90 minutes and layers were separated. The organic layer was washed with water, dried and distilled under vacuum to obtain a residue. The residue was treated with heptane (1500 ml), filtered and dried under vacuum at 50-55° C. to obtain the title compound. (Yield: 162 g, HPLC Purity: 99%)

Example 3

Preparation of N-[2-iodo-4-(2-methylsulfamoyl-ethyl)-phenyl]-acetamide

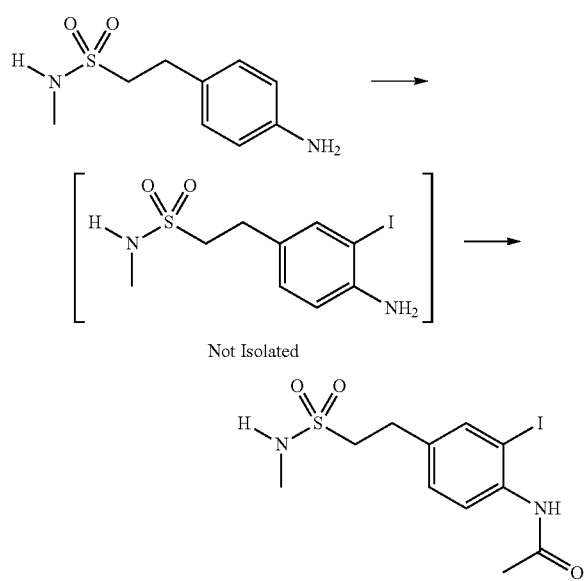

Not Isolated

To a solution of 2-(4-aminophenyl)ethane sulfonic acid methylamide (50 g) in dichloromethane (500 ml), a 10% solution of sodium bicarbonate (500 ml) was added at 25° C. so as to obtain a biphasic reaction mass. Iodine crystals were added slowly maintaining the temperature below 30° C. The mixture was agitated at 25° C. for about an hour and cooled to 10-15° C. The excess of iodine content in the mixture was neutralized with saturated sodium metabisulphite solution and a solution of 2-(4-amino-3-iodo-phenyl)-ethanesulfonic acid methylamide (75 g) in dichloromethane (750 ml) was added followed by dropwise addition of 50% solution of acetic anhydride in dichloromethane (300 ml) maintaining the temperature of 25° C. The reaction mass was stirred for about 90 minutes and layers were separated. The organic layer was washed with water, dried and distilled under vacuum to obtain a residue. The residue was stirred in heptane (500 ml), filtered and dried under vacuum at 50-55° C. to obtain the title compound. (Yield: 85 g, HPLC Purity: 99%)

Example 4

Preparation of 2-(4-benzylamino-3-iodo-phenyl)-ethanesulfonic Acid Methylamide

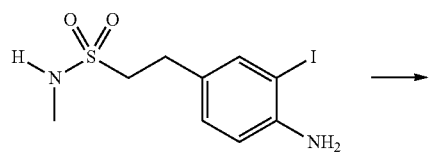

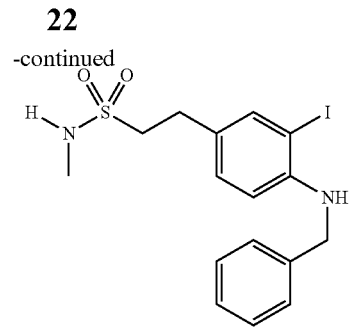

To a solution of 2-(4-amino-3-iodo-phenyl)-ethane-sulfonic acid methylamide (100 g) in anhydrous methanol (500 ml), a solution of benzaldehyde (46 g) in methanol (100 ml) was added dropwise maintaining temperature below 30° C. The reaction mass was stirred for 2-3 hours at 25° C. and sodium borohydride (12 g) was added over a period of 2 hours maintaining the temperature below 30° C. The reaction mass was stirred for about 2 hours at 25° C. Methanol was evaporated from the mixture and water (1000 ml) was added. The solution was extracted with dichloromethane (2000 ml). The organic layer was washed with water and distilled under vacuum to obtain a solid. The solid was treated with isopropyl alcohol (500 ml), filtered and dried under vacuum at 50-55° C. to obtain the title compound. (Yield: 116 g, HPLC Purity: 99%)

Example 5

Preparation of N-[4-(2-methylsulfamoyl-ethyl)-2-trimethylsilanylethynyl-phenyl]-acetamide

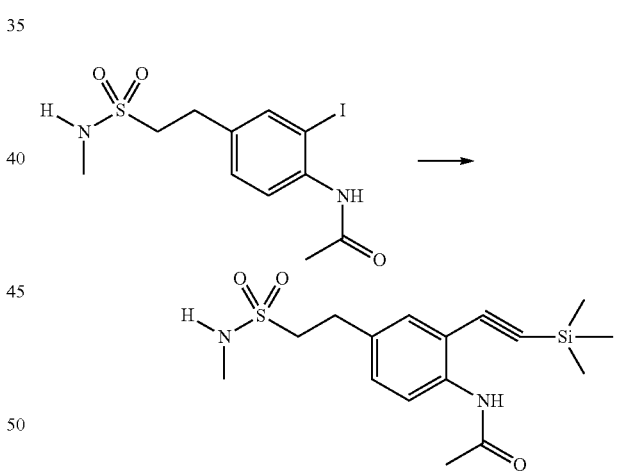

A solution of N-[2-iodo-4-(2-methylsulfamoyl-ethyl)-phenyl]-acetamide (100 g) in N,N-dimethyl formamide (500 ml) was prepared. To this solution, lithium chloride (49.8 g) and copper iodide (48.7 g) were added at 25° C. The reaction mixture was stirred for 30 minutes and Sonogashira Coupling Catalyst [Tetrakis triphenyl phosphonium Ligand] (1.2 g) was added. A solution ref trimethyl silyl acetylene in triethyl amine (49 ml in 90 ml) was added dropwise to the reaction mass at 25° C. The reaction mass was stirred for 30 minutes and cooled to 10° C. Water (250 ml) was added and pH of the reaction mass was adjusted to 4-5 with 50% acetic acid solution so as to obtain a solid. The solid so obtained was extracted with ethyl acetate, filtered through hyflo bed and distilled under vacuum to obtain a residue. The residue was treated with heptane (500 ml) for 4-5 hours, filtered and dried at 50-55° C. under vacuum to obtain the title compound. (Yield: 90 g. HPLC Purity: 95%)

Example 6

Preparation of 2-(4-benzylamino-3-trimethylsilanyl-ethynyl-phenyl)-ethanesulfonic acid methylamide

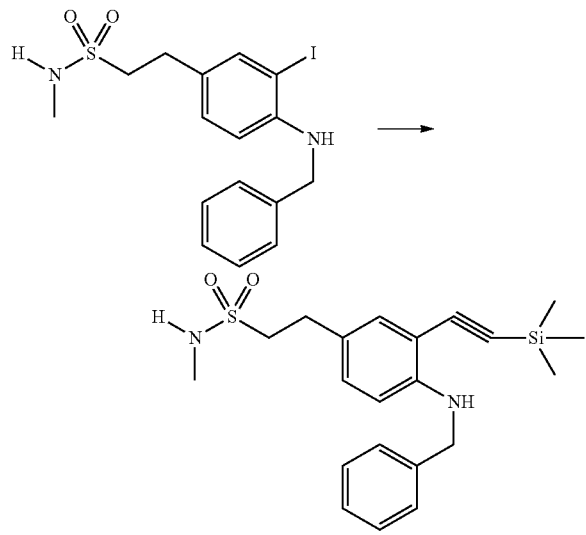

A solution of 2-(4-benzylamino-3-iodo-phenyl)-ethanesulfonic Acid Methylamide (100 g) in N,N-dimethyl formamide (500 ml) was prepared. To this solution, lithium chloride (56.70 gm) and copper iodide (54.87 g) were added at 25° C. The reaction mixture was stirred for 30 minutes and Sonogashira Coupling Catalyst [Tetrakis triphenyl phosphonium Ligand] (1.5 g) was added. A solution of trimethyl silyl acetylene in triethyl amine (56 ml in 105 ml) was added dropwise to the reaction mass at 25° C. The reaction mass was stirred for 30 minutes and cooled to 10° C. Water (500 ml) was added and pH of the reaction mass was adjusted to 4-5 with 50% acetic acid solution so as to obtain a solid. The solid so obtained was extracted with ethyl acetate, filtered through hyflo bed and distilled under vacuum to obtain a residue. The residue was treated with heptane (1000 ml) for 4-5 hours, filtered and dried at 50-55° C. under vacuum to obtain the title compound. (Yield: 82 g, HPLC Purity: 97%)

Example 7

Preparation of N-[2-ethynyl-4-(2-methylsulfamoyl-ethyl)-phenyl]-acetamide

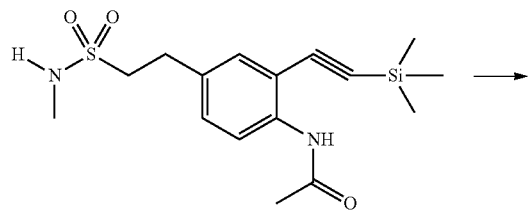

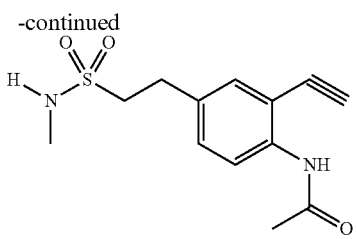

N-[4-(2-methylsulfamoyl-ethyl)-2-trimethylsilanylethynyl-phenyl]-acetamide (100 g) was dissolved in ethanol (1000 ml) at 25° C. and cooled to 15-20° C. Potassium hydroxide (20 gm) was added slowly maintaining temperature below 25° C., stirred for 2-3 hours and cooled to 10-15° C. pH of the reaction mixture was adjusted to 5 with 10% dilute HCl and concentrated under vacuum below 40° C. to obtain a residue. The residue was dissolved in water (250 ml) and extracted with dichloromethane (2000 ml). The organic layer was washed with water and concentrated under vacuum to obtain a residue. The residue was treated with heptane (200 ml) to obtain a solid which was filtered and dried under vacuum at 50-55° C. for 12 hours. (Yield: 70 g, HPLC Purity: 99%)

Example 8

Preparation of 2-(4-benzylamino-3-ethynyl-phenyl)-ethanesulfonic Acid Methylamide 2-(4-benzylamino-3-trimethylsilanylethynyl-phenyl)-ethanesulfonic acid methylamide (100 g) was dissolved in ethanol (1000 ml) at 25° C. and cooled to 15-20° C. Potassium hydroxide (20 g) was added slowly maintaining temperature below 25° C., stirred for 2-3 hours and cooled to 10-15° C. pH of the reaction mixture was adjusted to 5 with 10% dilute HCl and concentrated under vacuum below 40° C. to obtain a residue. The residue was dissolved in water (300 ml) and extracted with dichloromethane (2500 ml). The organic layer was washed with water and concentrated under vacuum to obtain a residue. The residue was treated with heptane (400 ml) to obtain a solid which was filtered and dried under vacuum at 50-55° C. for 12 hours. (Yield: 75 g, HPLC Purity: 98%)

Example 9

Preparation of 2-(1H-indol-5-yl)-ethanesulfonic Acid Methylamide

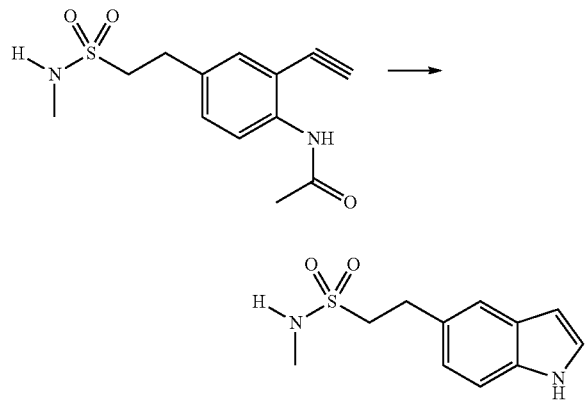

N-[2-ethynyl-4-(2-methylsulfamoyl-ethyl)-phenyl]-acetamide (100 g) was dissolved in N-methylpyrrolidone (900 ml) at 25° C. Potassium tert-butoxide (60 g) was added and the reaction mass was heated to 80-85° C. for 120-150 minutes. The reaction mass was cooled gradually to 25° C., water (3000 ml) was added and stirred for 30 minutes. The solution was extracted with ethyl acetate (2000 ml). The organic layer was dried over sodium sulfate and distilled under vacuum to obtain a residue. The residue was treated with heptane (300 ml) to obtain a solid which was filtered, washed with heptane and dried at 50-55° C. under vacuum to obtain the title compound. (Yield: 84 g, HPLC Purity: 98%)

Example 10

Preparation of 2-(1-benzyl-1H-indol-5-yl)-ethanesulfonic Acid Methylamide

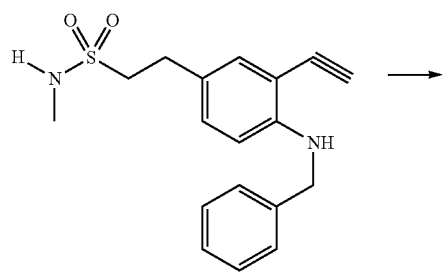

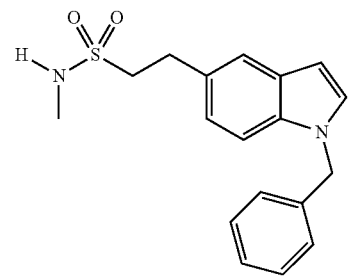

2-(4-benzylamino-3-ethynyl-phenyl)-ethanesulfonic acid methylamide (100 g) was dissolved in N-methylpyrrolidone (1500 ml) at 25° C. Potassium tert-butoxide (67 g) was added and the reaction mass was heated to 80-85° C. for 120-150 minutes. The reaction mass was cooled gradually to 25° C., water (3500 ml) was added and stirred for 30 minutes. The solution was extracted with ethyl acetate (4000 ml). The organic layer was dried over sodium sulfate and distilled under vacuum to obtain a residue. The residue was treated with heptane (500 ml) to obtain a solid which was filtered, washed with heptane and dried at 50-55° C. under vacuum to obtain the title compound. (Yield: 76 g, HPLC Purity: 98%)

Example 11

Preparation of 2-(1H-indol-5-yl)-ethanesulfonic Acid Methylamide

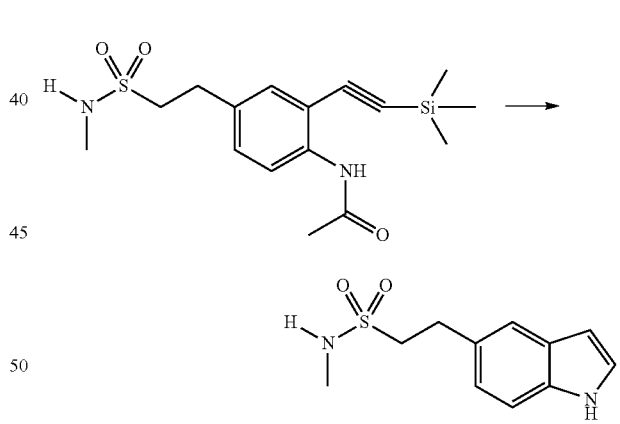

N-[4-(2-methylsulfamoyl-ethyl)-2-trimethylsilanylethynyl-phenyl]-acetamide (100 gm) was dissolved in N-methylpyrrolidone (900 ml) at 25° C. under inert atmosphere. Potassium tert-butoxide (49 g) was added and heated to 80-85° C. for 120-150 minutes. The reaction mass was cooled gradually to 25° C., water (3000 ml) was added and stirred for 30 minutes. The solution was extracted with ethyl acetate (2000 ml). The organic layer was dried over sodium sulfate and vacuum distilled to obtain a residue. The residue was treated with heptane (300 ml) to obtain a solid. The solid was filtered, washed with heptane and dried at 50-55° C. under vacuum to obtain title compound. (Yield: 74 g, HPLC Purity: 98%)

Example 12

Preparation of 2-[3-(1-methyl-1,2,3,6-tetrahydro-pyridin-4-yl)-1H-indol-5-yl]-ethanesulfonic Acid Methylamide

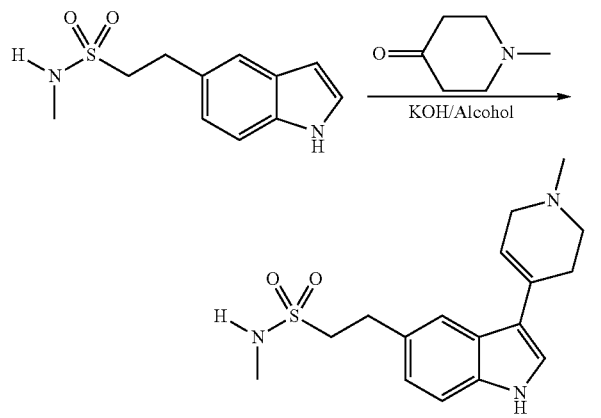

2-(1H-indol-5-yl)-ethanesulfonic acid methylamide (100 g) was dissolved in methanol (1000 ml) and N-methyl-4-piperidone (200 ml) was added thereto at 25° C. The reaction mass was stirred for 15 minutes and potassium hydroxide (300 g) was added at 25° C. The reaction mass was heated to 60-65° C. for 8 hours and cooled gradually to 25° C. Water (1500 ml) was added slowly and stirred the mixture till solid was obtained. The solid was filtered and dried at 50-55° C. under vacuum to obtain the title compound. (Yield: 80 g, HPLC Purity: 99%)

Example 13

Preparation of 2-[3-(1-methyl-1,2,3,6-tetrahydro-pyridin-4-yl)-1H-indol-5-yl]-ethanesulfonic Acid Methylamide

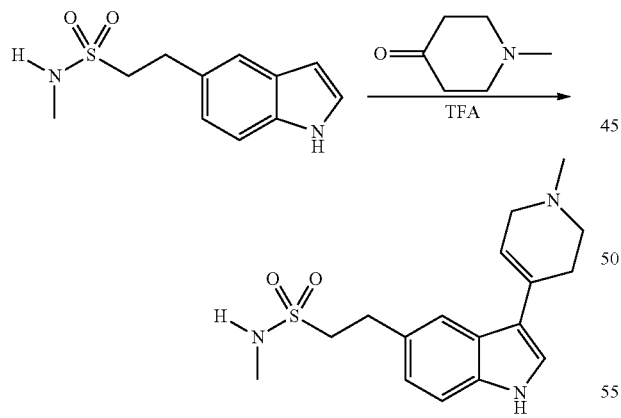

2-(1H-indol-5-yl)-ethanesulfonic acid methylamide (100 g) was dissolved in ethanol (1000 ml) and N-methyl-4-piperidone (200 ml) was added thereto at 25° C. and a solution of trifluoroacetic acid in ethanol (10 ml in 100 ml) was added over a period of 1 hour. The reaction mass was refluxed for 18-24 hours and cooled to 40° C. The reaction mass was concentrated under vacuum to obtain a residue and water (1500 ml) was added. The mixture was cooled to 10-15° C. and pH of the reaction mass was adjusted to 8 using 5% sodium bicarbonate solution and stirred. The resulting solid was filtered and dried at 50-55° C. under vacuum to obtain title compound (Yield: 93 g, HPLC Purity: 99%)

Example 14

Preparation of 2-[1-benzyl-3-(1-methyl-1,2,3,6-tetrahydro-pyridin-4-yl)-1H-indol-5-yl]-ethanesulfonic Acid Methylamide

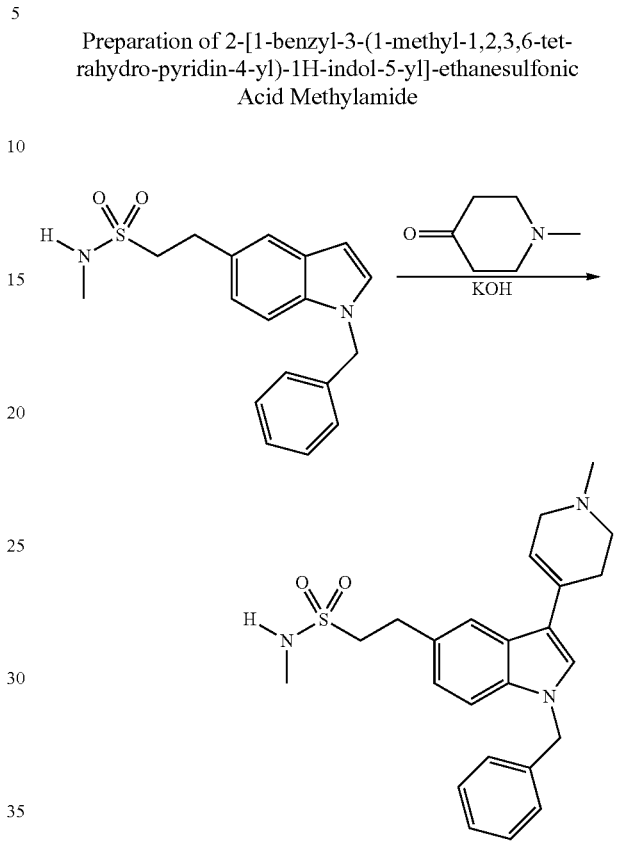

2-(1-benzyl-1H-indol-5-yl)-ethanesulfonic acid methylamide (100 g) was dissolved in methanol (1000 ml) and N-methyl-4-piperidone (100 ml) was added thereto at 25° C. The reaction mass was stirred for 15 minutes and potassium hydroxide (200 g) was added at 25° C. The reaction mass was heated to 60-65° C. for 8 hours and cooled gradually to 25° C. Water (2500 ml) was added slowly and stirred the mixture till solid is obtained. The solid was filtered and dried at 50-55° C. under vacuum to obtain the title compound (Yield: 98 g, HPLC Purity: 99%).

Example 15

Preparation of 2-[3-(1-methyl-piperidin-4-yl)-1H-indol-5-yl]-ethanesulfonic Acid Methylamide (Naratriptan)

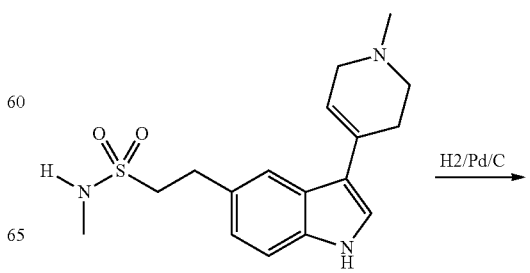

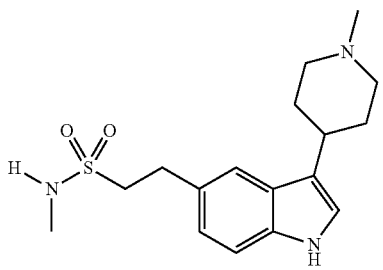

A solution of 2-[3-(1-methyl-1,2,3,6-tetrahydro-pyridin-4-yl)-1H-indol-5-yl]-ethanesulfonic acid methylamide (100 gm) in acetic acid (1500 ml) was prepared and 50% wet 10% palladium on charcoal (5 g) was added under stifling at 25° C. in Hydrogenation vessel. The Hydrogenation vessel was evacuated with vacuum and a hydrogen pressure of 28-42 psi at 25° C. was applied till the hydrogen intake was ceased to zero. The reaction mass was filtered under inert atmosphere and the filtrate was subjected to vacuum distillation to obtain a residue which was dissolved in water (1000 ml). The solution was washed with ethyl acetate (900 ml) and the layers were separated. The aqueous layer was cooled to 10° C. and basified with liq. ammonia till pH 7.5-8.5. The aqueous layer was extracted with Ethyl Acetate (2000 ml), filtered, distilled under vacuum till half of its total initial volume and cooled gradually to 25° C. to obtain a solid. The solid was filtered and dried at 40-50° C. under vacuum for 12 hours to obtain the title compound. (Yield: 82 g, HPLC Purity: 99%)

Example 16

Preparation of 2-[3-(1-methyl-piperidin-4-yl)-1H-indol-5-yl]-ethanesulfonic Acid Methylamide (Naratriptan)

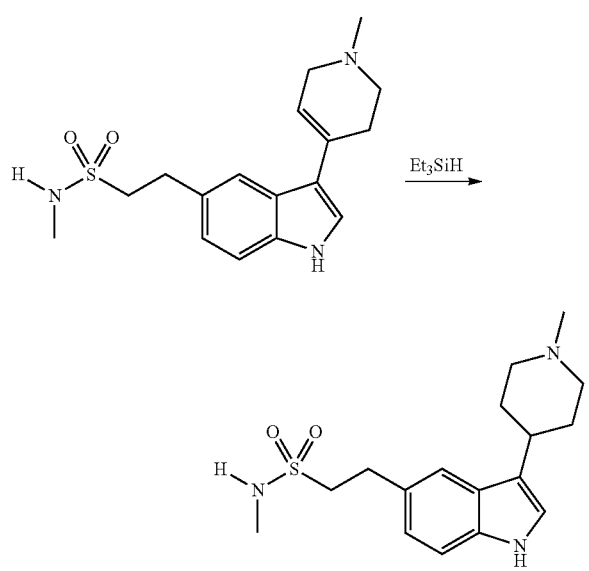

A solution of 2-[3-(1-methyl-1,2,3,6-tetrahydro-pyridin-4-yl)-1H-indol-5-yl]-ethanesulfonic acid methylamide (100 g) in dichloromethane (1000 ml) was prepared. Trifluoroacetic acid (10 ml) was added under stifling at 25° C. and stirred for 10 minutes. A separately prepared solution of triethyl silane in dichloromethane (200 mil in 250 ml) was added over a period of 3-4 hours below 30° C. The reaction mass was stirred overnight at 25° C. and cooled to 10-15° C. A 5% aqueous bicarbonate solution was added dropwise. The organic layer was washed with water and evaporated to afford a residue. The residue so obtained was triturated in ethyl acetate (700 ml) to obtain a solid which was filtered and dried at 40-50° C. for 12 hours under vacuum to obtain the title compound (Yield: 79 g, HPLC Purity: 99%).

Example 17

Preparation of 2-[1-benzyl-3-(1-methyl-piperidin-4-yl)-1H-indol-5-yl]-ethanesulfonic Acid Methylamide

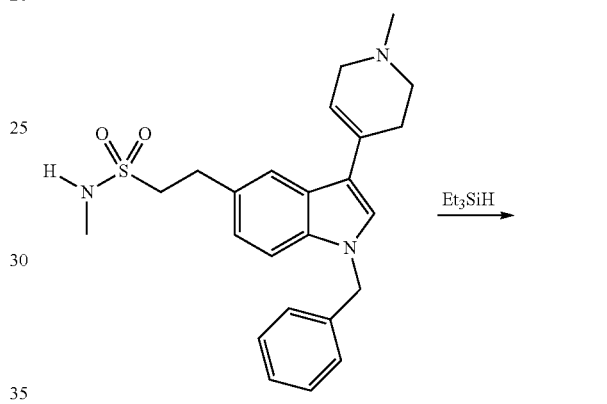

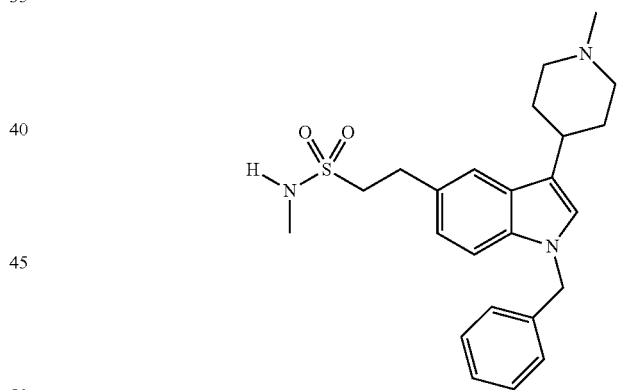

A solution of 2-[1-benzyl-3-(1-methyl-1,2,3,6-tetrahydro-pyridin-4-yl)-1H-indol-5-yl]-ethanesulfonic acid methylamide (100 g) in dichloromethane (1000 ml) was prepared followed by addition of trifluoroacetic acid (10 ml) under stifling at 25° C. The reaction mass was stirred for 10 minutes and a separately prepared solution of triethyl silane in dichloromethane (200 ml in 250 ml) was added over a period of 3-4 hours below 30° C. The reaction mass was stirred overnight at 25° C. and cooled to 10-15° C. A 5% aqueous bicarbonate solution was added dropwise. The organic layer was washed with water and evaporated to afford a residue. The residue so obtained was triturated in ethyl acetate (1000 ml) to obtain a solid which was filtered and dried at 40-50° C. for 12 hours under vacuum to obtain the title compound (Yield: 85 g, HPLC Purity: 99%)

Example 18

Preparation of 2-[3-(1-methyl-piperidin-4-yl)-1H-indol-5-yl]-ethanesulfonic Acid Methylamide (Naratriptan)

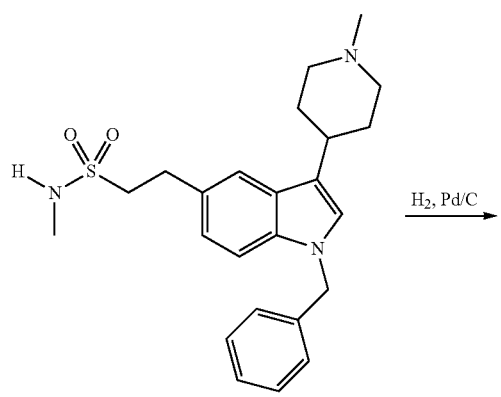

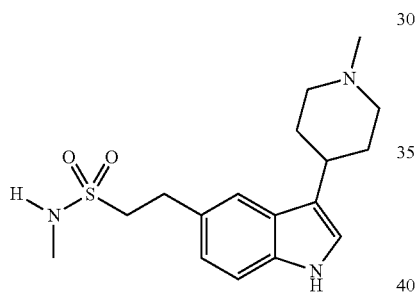

A solution of 2-[1-benzyl-3-(1-methyl-piperidin-4-yl)-1H-indol-5-yl]-ethanesulfonic acid methylamide (100 gm) in acetic acid (3000 ml) was prepared and 50% wet 10% palladium on charcoal (5 g) was added under stirring at 25° C. in Hydrogenation vessel. The Hydrogenation vessel was evacuated with vacuum and a hydrogen pressure of 14 psi at 25° C. was applied till the hydrogen intake was ceased to zero. The reaction mass was filtered under inert atmosphere and the filtrate was subjected to vacuum distillation to obtain a residue which was dissolved in water (3000 ml) The solution was washed with ethyl acetate (1500 ml) and the layers were separated. The aqueous layer was cooled to 10° C. and basified with liq. ammonia till pH 7.5-8.5. The aqueous layer was extracted with ethyl acetate (3500 ml) and cooled to 10° C. and basified with liq. ammonia till pH 7.5-8.5. The aqueous layer was extracted with ethyl acetate (3500 ml), filtered and vacuum distilled till half of its total initial volume. Cooled gradually to 25° C. to obtain a solid which was filtered and dried at 40-50° C. for 12 hours under vacuum to obtain the title compound. (Yield: 70 g., HPLC Purity: 98%)

Example 19

Preparation of 2-[3-(1-methyl-piperidin-4-yl)-1H-indol-5-yl]-ethanesulfonic Acid Methylamide (Naratriptan)

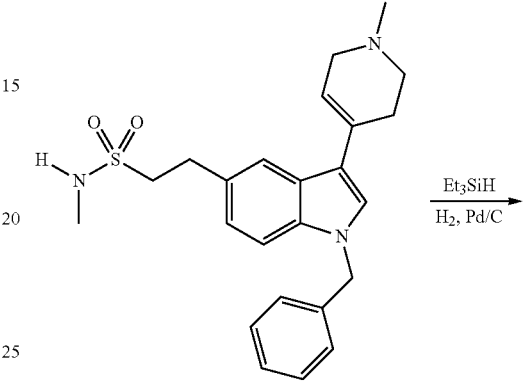

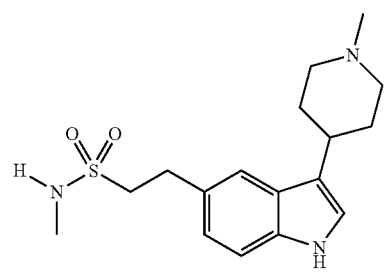

A solution of 2-[1-benzyl-3-(1-methyl-1,2,3,6-tetrahydro-pyridin-4-yl)-1H-indol-5-yl]-ethanesulfonic acid methylamide (100 gm) in ethanol (3000 ml) was prepared and 50% wet 10% palladium on charcoal (5 g) was added under stifling at 25° C. followed by slow addition of triethyl silane (450 ml) over a period of 3-4 hours below 30° C. The reaction mass was stirred overnight at 25° C. and filtered under inert atmosphere. The filtrate was subjected to vacuum distillation so as to obtain a residue which was treated with water (2000 ml) and cooled to 10-15° C. The pH of the reaction mass was adjusted to 1 using 5% dilute hydrochloric acid to obtain a clear solution. The solution was washed with of ethyl acetate (500 ml). The aqueous layer was cooled to 10° C. and basified with liq. ammonia till pH 7.5-8.5. The aqueous layer was extracted with ethyl acetate (1500 ml), filtered, distilled under vacuum till half of its total initial volume and cooled gradually to 25° C. to obtain a solid. The solid was filtered and dried at 40-50° C. for 12 hours under vacuum to obtain the title compound. (Yield: 60 g, HPLC Purity: 99%)

Example 20

Preparation of 2-[3-(1-methyl-piperidin-4-yl)-1H-indol-5-yl]-ethanesulfonic Acid Methylamide Hydrochloride (Naratriptan Hydrochloride)

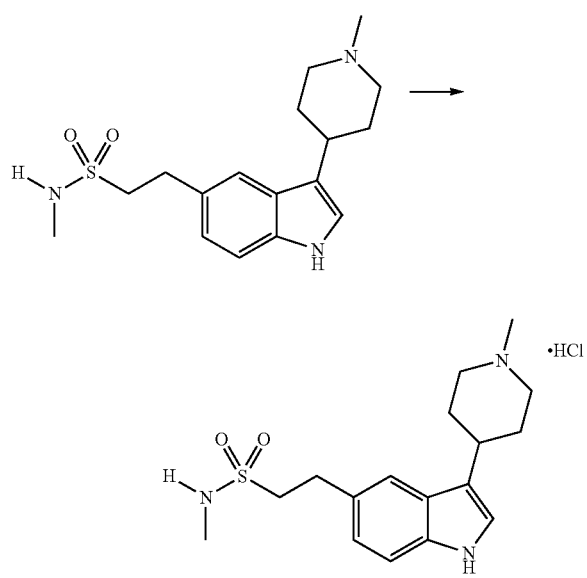

2-[3-(1-Methyl-piperidin-4-yl)-1H-indol-5-yl]-ethanesulfonic acid methylamide (Naratriptan base) (100 g) was dissolved in methanol (1500 ml) under stifling for 30 minutes to obtain a clear solution. The reaction mass was cooled to 5-10° C. and 20% aqueous hydrochloric acid was added till the pH of the reaction mass was adjusted to 1.0. The temperature of the reaction mass was raised to 25° C. and filtered. The solid was dried in vacuum chamber at 50-55° C. to obtain the title compound. (Yield: 90 g, HPLC Purity: 99.69%)

Example 21

Preparation of 2-[3-(1-Methyl-piperidin-4-yl)-1H-indol-5-yl]-ethanesulfonic acid methylamide Hydrochloride (Naratriptan Hydrochloride)

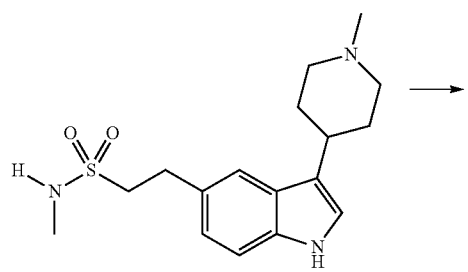

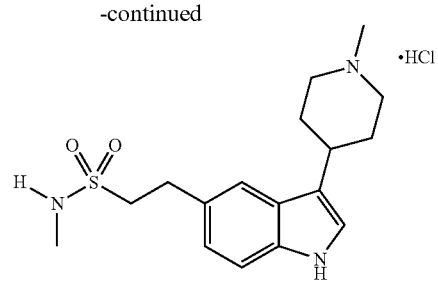

2-[3-(1-Methyl-piperidin-4-yl)-1H-indol-5-yl]-ethanesulfonic acid methylamide i.e. (Naratriptan base) (100 gm) was dissolved in acetone (1000 ml) under stirring for 30 minutes to obtain a clear solution. The reaction mass was cooled to 5-10° C. and pH of the reaction mass was adjusted to 1.0 with 20% IPA-HCl solution. The temperature of the reaction mass was raised to 25° C. and filtered. The solid was dried in vacuum chamber at 50-55° C. to obtain the title compound. (Yield: 95 g, HPLC Purity: 99.56%)

It will be appreciated that the invention may be modified within the scope of the appended claims.

The invention claimed is:

1. A process for preparing naratriptan comprising: (a) reacting a compound of formula (3) with a compound of the formula HCCR

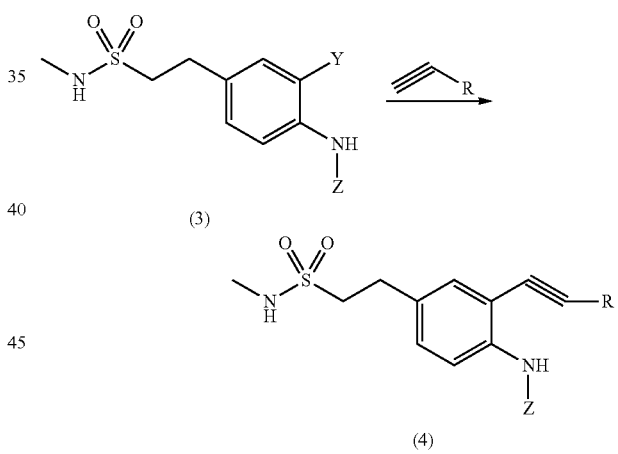

wherein Z is a protecting group, Y is a leaving group and R is a trialkyl silyl group, a trialkylstannyl group or a zinc (II) halide, to obtain the compound of formula (4); (b) converting the compound of formula (4) to a compound of formula (5)

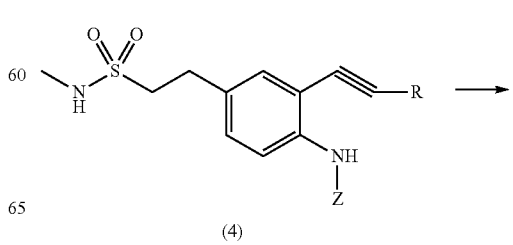

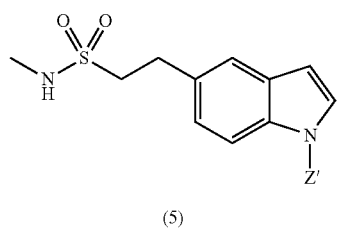

(5)

wherein Z' is hydrogen or a benzyl group, (c) converting the compound of formula (5) to naratriptan; and (d) optionally converting naratriptan to a salt thereof

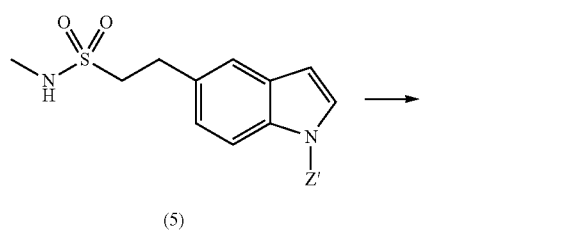

(5)

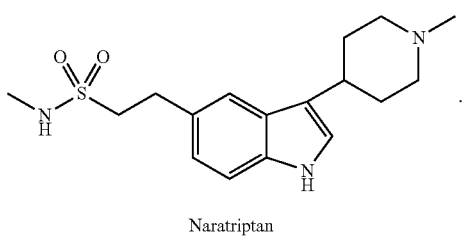

Naratriptan

2. The process according to claim 1, wherein the compound HCCR is selected from the group consisting of ethyl (ethynyl) dimethyl silane, trimethylsilyl acetylene, triethyl (ethynyl) silane, diethyl (ethynyl )methyl silane, ethyl (ethynyl) dimethyl stannane, diethyl (ethynyl) methyl stannane, (ethynyl) trimethyl stannane and ethynyl zinc (II) halide.

3. The process according to claim 1, wherein Z is selected from the group consisting of acetyl, trifluoroactyl, BOC, benzoyl, benzyloxy carbonyl and benzyl.

4. The process according to claim 1, wherein Y is selected from the group consisting of chloro, bromo, iodo, OTf (triflate) and OTs (tosylate).

5. The process according to claim 1, wherein step (a) is carried out in the presence of a palladium-phosphine complex and optionally in the presence of a copper (I) halide and lithium halide.

6. The process according to claim 5, wherein the Pd-phosphine complex is tetrakistriphenylphosphine Pd (0).

7. The process according to claim 1, wherein Z is a protecting group other than benzyl, Z' is hydrogen and the conversion of compound (4) to compound (5) comprises deprotection of group Z and cyclisation.

8. The process according to claim 7, wherein the deprotection is carried out using tetrabutylammonium halide or an acid selected from acetic acid, trifluoroacetic acid, dilute sulfuric acid, dilute hydrochloric acid and dilute nitric acid.

9. The process according to claim 1, wherein the conversion of compound (4) to compound (5) comprises cyclising compound (4) in the presence of a base and a solvent.

10. The process according to claim 1, wherein conversion of compound (5) to naratriptan comprises reacting compound (5) with N-methyl-4-piperidone to form a compound of formula (6) and converting compound (6) to naratriptan

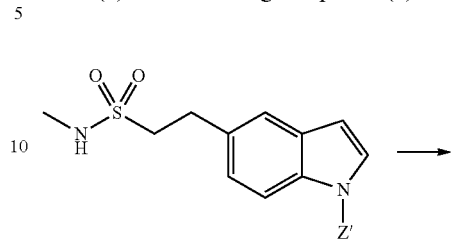

(5)

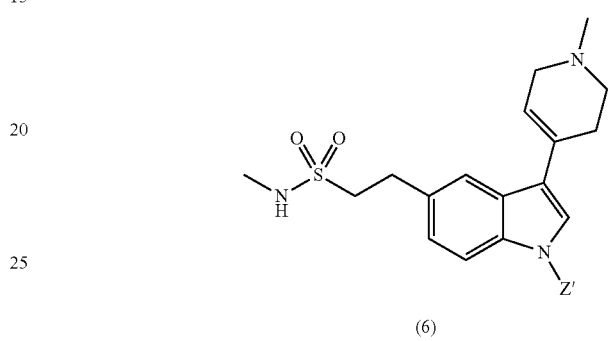

(6)

11. The process according to claim 10, wherein Z' is hydrogen and the conversion of compound (6) to naratriptan comprises catalytic hydrogenation in the presence of a catalyst selected from the group consisting of palladium, palladium hydroxide, palladium on activated carbon, palladium on alumina, platinum, platinum on activated carbon, ruthenium, rhodium and Raney nickel.

12. The process according to claim 10, wherein Z' is hydrogen and the conversion of compound (6) to naratriptan comprises organic reduction.

13. The process according to claim 12, wherein the organic reduction is carried out using a trialkyl silane, preferably triethyl silane.

14. The process according to claim 10, wherein Z' is benzyl and the conversion of compound (6) to naratriptan comprises organic reduction.

15. The process according to claim 14, wherein compound (6) is first reduced by organic reduction in situ to obtain compound (7) which further undergoes catalytic hydrogenation to obtain naratriptan

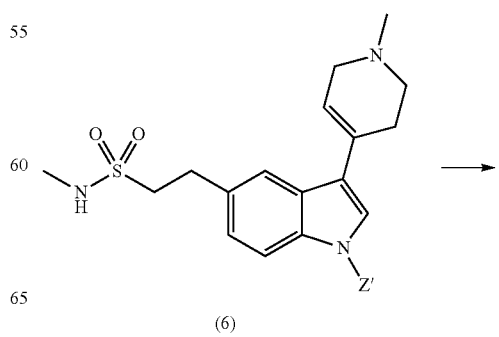

(6)

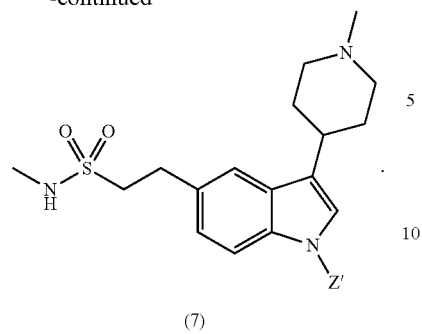
(7)
16. A compound of formula (4)
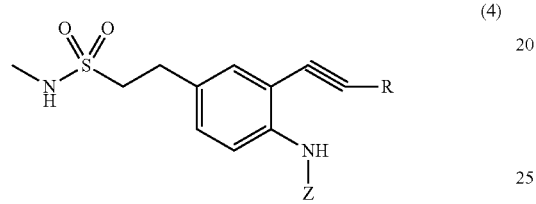
(4)
wherein Z is selected from the group consisting of acetyl, trifluoroactyl, BOC, benzoyl, benzyloxy carbonyl and benzyl, and R is selected from the group consisting of trimethylsilyl, —Sn(Bu)$_3$ or —ZnBr.
* * * * *

UNITED STATES PATENT AND TRADEMARK OFFICE
CERTIFICATE OF CORRECTION

PATENT NO.       : 8,735,589 B2                                    Page 1 of 1
APPLICATION NO.  : 13/390455
DATED            : May 27, 2014
INVENTOR(S)      : Rao et al.

It is certified that error appears in the above-identified patent and that said Letters Patent is hereby corrected as shown below:

In the Specification

Column 29, Line 18, replace "stifling" with --stirring--
Column 29, Line 67, replace "stifling" with --stirring--
Column 30, Line 57, replace "stifling" with --stirring--
Column 32, Line 48, replace "stifling" with --stirring--
Column 33, Line 37, replace "stifling" with --stirring--

Signed and Sealed this
Twenty-ninth Day of July, 2014

Michelle K. Lee
*Deputy Director of the United States Patent and Trademark Office*